(12) United States Patent
Righetti et al.

(10) Patent No.: US 12,414,758 B2
(45) Date of Patent: Sep. 16, 2025

(54) NON-INVASIVE ESTIMATION OF MATERIAL PARAMETERS

(71) Applicant: The Texas A&M University System, College Station, TX (US)

(72) Inventors: Raffaella Righetti, College Station, TX (US); Md Tauhidul Islam, College Station, TX (US)

(73) Assignee: The Texas A&M University System, College Station, TX (US)

( * ) Notice: Subject to any disclaimer, the term of this patent is extended or adjusted under 35 U.S.C. 154(b) by 533 days.

(21) Appl. No.: 17/607,787

(22) PCT Filed: May 9, 2020

(86) PCT No.: PCT/US2020/032262
§ 371 (c)(1),
(2) Date: Oct. 29, 2021

(87) PCT Pub. No.: WO2020/231876
PCT Pub. Date: Nov. 19, 2020

(65) Prior Publication Data
US 2022/0218310 A1    Jul. 14, 2022

Related U.S. Application Data

(60) Provisional application No. 62/846,191, filed on May 10, 2019, provisional application No. 62/846,216, (Continued)

(51) Int. Cl.
*A61B 8/00* (2006.01)
*G06F 17/11* (2006.01)
*G06T 7/00* (2017.01)

(52) U.S. Cl.
CPC .............. *A61B 8/485* (2013.01); *G06F 17/11* (2013.01); *G06T 7/0012* (2013.01); *G06T 2207/10132* (2013.01); *G06T 2207/30096* (2013.01)

(58) Field of Classification Search
CPC .......................... G01S 7/52042; A61B 8/485
See application file for complete search history.

(56) References Cited

U.S. PATENT DOCUMENTS

2005/0004466 A1* 1/2005 Hynynen ............ G01S 15/8977
600/449
2008/0306384 A1* 12/2008 Boctor ................... A61B 8/485
600/443

(Continued)

FOREIGN PATENT DOCUMENTS

WO    2020231876 A1    11/2020

OTHER PUBLICATIONS

Islam, et al.; "Non-invasive imaging of Young's modulus and Poisson's ratio in cancers in vivo"; https://arxiv.org/ftp/arxiv/papers/1809/1809.02929.pdf; Sep. 9, 2018; 37 pgs.

(Continued)

*Primary Examiner* — Rajeev P Siripurapu

(57) ABSTRACT

The disclosure provides a method, a system, an apparatus, and a computer program product for determining IFP, IFV, and fluid flow inside tumors. In one example, a method for estimating tumor parameters is disclosed. This method includes: (1) receiving image data from a tumor, (2) obtaining strain data of the tumor from the image data, and (3) determining a tumor parameter, such as IFP and IFV, employing the strain data and an analytical model. Additional tumor parameters can be determined employing the strain data and other analytical models. The additional tumor parameters include compression-induced fluid pressure, velocity and flow inside the tumor, parameter ? employing (Continued)

the fluid pressure, the ratio between vascular permeability and interstitial permeability, and the ratio of peak IFP and effective vascular pressure. Each of these parameters can be employed for analyzing, monitoring, treating, testing, etc., tumors or the effects of drugs on the tumors.

16 Claims, 5 Drawing Sheets

Related U.S. Application Data filed on May 10, 2019, provisional application No. 62/846,241, filed on May 10, 2019.

(56) References Cited

U.S. PATENT DOCUMENTS

| | | |
|---|---|---|
| 2010/0049451 A1 | 2/2010 | Lu et al. |
| 2011/0060222 A1* | 3/2011 | Thittai .................. A61B 8/485 600/438 |
| 2016/0140730 A1 | 5/2016 | Falahatpisheh et al. |

OTHER PUBLICATIONS

Aslanidou, et al.; "Co-Localization of Microstructural Damage and Excessive Mechanical Strain at Aortic Branches in Angiotensin-II Infused Mice"; Biomechanics and Modeling in Mechanobiology; Apr. 7, 2019; https://biblip.urgent.be/publication/8624916/file/8624918.pdf; 39 pgs.

* cited by examiner

NON-INVASIVE ESTIMATION OF MATERIAL PARAMETERS

CROSS-REFERENCE TO RELATED APPLICATION

This application is the National Stage of, and therefore claims the benefit of, International Application No. PCT/US2020/032262 filed on May 9, 2020, entitled "NON-INVASIVE ESTIMATION OF MATERIAL PARAMETERS," which was published in English under International Publication Number WO 2020/231876 on Nov. 19, 2020, which claims the benefit of U.S. Provisional Application Ser. No. 62/846,191, filed May 10, 2019, U.S. Provisional Application Ser. No. 62/846,216, filed May 10, 2019, and U.S. Provisional Application Ser. No. 62/846,241, filed May 10, 2019. The above applications are commonly assigned with this National Stage application and are incorporated herein by reference in their entirety.

TECHNICAL FIELD

This application is directed, in general, to estimating material parameters and, more specifically, to the non-invasive assessment of mechanical and transport parameters inside materials, for example tissues such as tumors.

BACKGROUND

Understanding tissue parameters can be beneficial in treating patients. For example, various parameters can be used to describe the mechanical behavior of tumors and other tissues, and can also indicate changes as the mechanical properties of tissues are altered due to a disease, such as cancer, atherosclerosis, fibrosis of the liver, etc. Young's modulus (YM) and Poisson's ratio (PR) are examples of mechanical parameters that can be useful in the diagnosis, prognosis, and treatment of diseases. Young's modulus (YM) and Poisson's ratio (PR) can also be useful in understanding and predicting the behavior of non-biological materials.

Interstitial permeability and vascular permeability are also valuable material parameters that can be useful in understanding tumors. Both interstitial permeability and vascular permeability of a tumor can affect drug delivery to the tumor through modifying the convection and consolidation times of drug molecules inside the tumor. Solid stress (SSg) can also be a beneficial material parameter.

SSg inside a tumor can be divided in three main categories: stress exerted on the tumor by the surrounding host tissue also called "externally applied stress", "swelling stress" and growth-induced or "residual stress." The externally applied SSg is generated by the tissue surrounding the tumor as a consequence of cells within tumors growing and producing new solid material-cells and matrix fibers, which push against the surrounding host tissue to expand. The surrounding tissue, in turn, resists the expansion by exerting a stress on the tumor. Swelling SSg is related to a phenomenon called chemical expansion. The interstitial space of many tumors may have a high concentration of negatively charged hyaluronan chains. The repulsive electrostatic force among these negative charges may cause swelling in the tumor. In general terms, the residual SSg may be defined as the remaining stress inside a body, when all external loads on the body have been removed.

BRIEF DESCRIPTION

Reference is now made to the following descriptions taken in conjunction with the accompanying drawings, in which.

DETAILED DESCRIPTION

Figure 1:
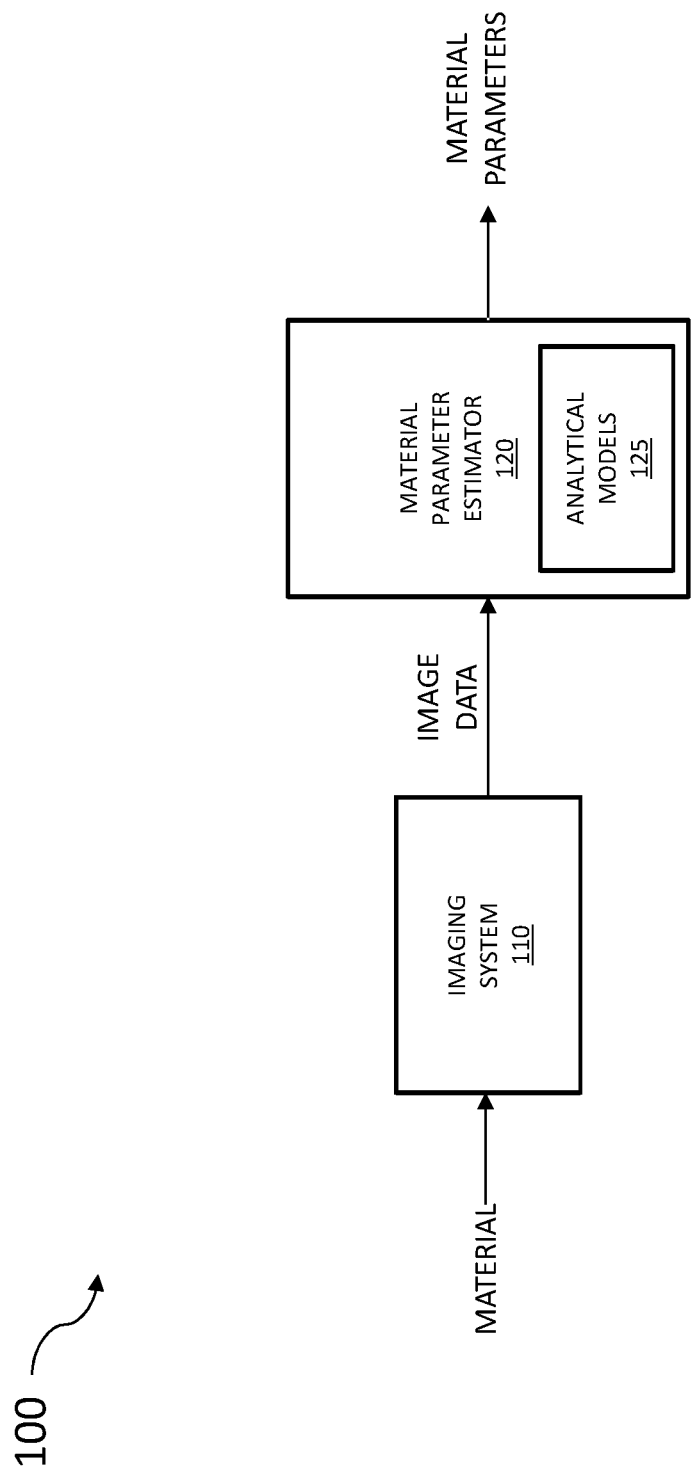
FIG. 1 illustrates a block diagram of an example of a system constructed according to the principles of the disclosure.

Included herein are techniques or methods, an apparatus, and system to estimate material parameters using strain data from the material. The material parameters include mechanical and transport parameters of a material. Techniques disclosed herein use the strain data and analytical models to provide new, non-invasive tools to assess mechanical and transport parameters in materials, such as biological tissues including tumors. A tumor is a mass of tissue that can be benign or malignant. As such, the tumor can be cancer. The tumor can be from a sample that has been removed from a host or can still be with the host, i.e., unremoved. Accordingly, the strain data can be acquired employing ex vivo or in vivo measurements. The host can be a human or an animal.

A material is a biological or non-biological material. As noted above, a tissue, such as a tumor, is an example of a biological material. The techniques included herein can also be used to estimate tissue parameters in other materials or biological tissues that are not tumors such as musculoskeletal tissue, brain, kidney, liver and other tissues. The techniques included herein can also be used to estimate parameters of non-biological materials different than biological tissues such as man-made materials, minerals, soils, etc. Accordingly, the disclosure presents a three-dimensional method that allows reconstruction of both YM and PR based on an analytical model, such as based on Eshelby's inclusion formulation. The disclosed method overcomes the aforementioned limitations of current YM reconstruction methods. It allows simultaneous quantification and imaging of the YM and PR in both a tumor and surrounding tissue irrespective of the complex boundary conditions and/or the shape of the tumor and for a wide range of tumor/background YM contrasts, for example 0.1-50. The YM and PR are reconstructed from knowledge of the strain responses at steady state and the tumor and normal tissues can behave as, for example, poroelastic materials.

The strain data can be obtained from a material using an imaging method or can be obtained employing other methods used in the art. When using an imaging method, image data of a material is provided that corresponds to parameters of the material. From the acquired image data, the various parameters can be determined using the developed analytical models. The imaging method can be ultrasound, mammography, magnetic resonance imaging (MRI), computed tomography (CT), X-rays, optics, acoustics, photoacoustic imaging, etc. or a combination of imaging methods. In some embodiments disclosed herein, ultrasound is used as the imaging method. The imaging method can be part of a treatment or can be part of a testing process. For example, the image data can be obtained as part of a process to test the effect of drugs on a tissue.

The imaging method can be performed as part of an examination typically executed in clinical settings. Acquiring the image data can include compressing the tissue for a designated amount of time, while the imaging probe is in contact with the tissue. The compression time can vary depending on, for example, the imaging method and the tissue properties. Ultrasound elastography is an example of an imaging modality where compression is applied on a sample tissue and strain data is measured. Normal strain data of a tissue can be obtained from ultrasound elastography and employed in disclosed analytical models to estimate the various parameters.

The analytical models disclosed herein provide a relationship between the different material parameters and the strain data. The analytical models can be used with specific experimental set-ups, including but not limited to creep compression, stress relaxation, and sinusoidal excitations. For example, an analytical model can be used for tumors surrounded by background tissues wherein mechanopathological parameters are estimated using the strain data from the ultrasound experiment.

The disclosure provides a non-invasive technique that uses strain data and analytical models to determine mechanical and transport parameters in biological and non-biological materials. For example, the disclosure provides a non-invasive technique that uses strain data and analytical models to simultaneously reconstruct YM and PR of a tumor and of its surrounding tissues, irrespective of the shape and boundary conditions of the tumor. The disclosed methods can estimate the YM and PR of tumors in complex boundary conditions and for tumors of many different shapes such as sphere, ellipse, trigon, tetragon, pentagon, etc. The disclosed non-invasive method allows the generation of high spatial resolution YM and PR maps from strain data, such as axial and lateral strain data, obtained via, for example, an imaging method. In the disclosed approach, the tumor and normal tissues can behave as poroelastic materials, and the YM and PR are reconstructed from knowledge of the strain responses when the material is at steady state. A poroelastic material is, by definition, compressible. After the application of a stress, a poroelastic tissue behaves as an incompressible solid with PR of, for example, 0.5. Then, relaxation takes place inside the tissue during which dynamic processes occur, and the strain distributions inside the material undergo spatial and temporal changes. At steady state (also referred to as "drained" condition), the tissue behaves as a linear elastic solid. Therefore, YM and PR can be used to quantify the stiffness and compressibility of a tissue, such as a poroelastic tissue, as long as the measurements are computed for tissues in steady state conditions. Non-invasive techniques that use analytical models and strain data for estimating interstitial permeability, vascular permeability, and spatial distribution of the solid stress (SSg) are also disclosed.

Some of the advantages offered by the disclosed techniques include non-invasiveness, low cost, safety, non-radiation, portability, computational efficiency, etc. The disclosed techniques can also be used before or after different types of treatments such as vascular normalization, stress normalization, chemotherapy, immunotherapy, targeted drug delivery, etc. Additionally, the disclosed non-invasive technique can be integrated into multiple platforms such as computer program products, imaging systems, or dedicated devices, such as lab devices or lab equipment. Therefore, the technology can be made readily available for clinical applications in diagnostic systems, commercialized as a software package, and manufactured in a portable diagnostic and/or therapeutic device. The technology can also be made readily available for applications in non-medical systems, commercialized as a software package, and manufactured in a portable device. For example, a lab device can be configured, i.e., designed and constructed with the necessary logic, to employ the disclosed technology to quantify material properties or to test the efficacy of a drug or drugs on a tissue or a tumor.

FIG. 1 illustrates a block diagram of an example of a system 100 constructed according to the principles of the disclosure. The system 100 includes an imaging system 110 and a material parameter estimator 120. The imaging system 110 and the material parameter estimator 120 can be in separate computing devices as illustrated that can be communicatively coupled via conventional connections. In some examples, the imaging system 110 and the material parameter estimator 120 are integrated in a single computing device.

The imaging system 110 is configured to acquire image data of a material. The data of the material is non-invasively acquired and can be acquired without the use of an imaging contrast agent. The imaging system 110 can be an ultrasound system. The ultrasound system can have a single element, linear or two-dimensional transducers for obtaining data. In one example, ultrasound poroelastography is used to obtain the image data. Other imaging systems, such as photoacoustic imaging, mammography, computed tomography (CT) and magnetic resonance imaging (MRI), can also be employed.

The material parameter estimator 120 is configured to calculate one or more parameters of the material employing strain data of the material and an analytical model or models 125. The strain data can be determined from the image data provided by the imaging system 110. The strain data can also be provided by other conventional methods or procedures. Various methods can be employed for obtaining the strain data, such as sample tracking, correlation, optical flow estimation, block matching, Doppler-based processing, etc. The strain data can be the axial, lateral, elevational, or volumetric strain data. The analytical models 125 relate the material parameters to the strain data. The material parameters can be YM, PR, interstitial permeability, vascular permeability, and SSg. The analytical models 125 can be represented as an algorithm or algorithms in software that are employed in a computing device or a processor thereof to determine the material parameters. Once the material parameters are determined, the parameters can be employed for various medical, industrial, or research processes and procedures, such as the diagnosis, prognosis and treatment of diseases, and the testing of drugs. As such, the material parameters can be employed for the benefit of the host, others, or both. An example of equations that can be used for the analytical models 125 are provided below. The analytical models 125 can be located in a data storage of the material parameter estimator 120.

The material parameter estimator 120 can be configured to determine YM and PR of the material employing strain data and an analytical model, such as a cost function. The strain data can be or can include the axial strain and the lateral strain of the material. The cost function correlates the YM and the PR and the material parameter estimator 120 is configured to reconstruct the YM and the PR for the material by minimizing the cost function. The cost function and related equations can be represented as an algorithm in software wherein a computing device or a processor thereof is used to minimize the cost function to determine the YM and PR.

The cost function is represented by Equation 1.

$$J(E_i, v_i) = (J_1(E_i, v_i))^2 + (J_2(E_i, v_i))^2 \quad (1)$$

where $$J_1(E_i, v_i) = \epsilon_1^*(1) - \epsilon_2^*(1), J_2(E_i, v_i) = \epsilon_1^*(2) - \epsilon_2^*(2) \quad (2)$$

Here, $\in_1$ is defined as $$\epsilon = \epsilon^0 + S : \epsilon^*,$$

and $\in_2$ is defined as $$\epsilon^* = (S + A)^{-1} : (-\epsilon^0),$$

where $A = [C - C^0]^{-1} \cdot C^0$.

Here, C and $C^0$ are the stiffness matrix of the inclusion and background, respectively; S is the Eshelby's tensor and depends on geometry of the inclusion and Poisson's ratio of the background; and $\in^0$ is the strain in the background.

By minimizing the cost function J of Equation 1, YM ($E_i$) and PR ($v_i$) of an inclusion can be obtained. The YM and PR of the background can be determined from Equation 3

$$\sigma^0 = C^0 : \epsilon^0 \quad (3)$$

The expressions of $\in_1$ and $\in_2$ for elliptic (prolate, oblate) and spherical inclusions are known in the art along with the expressions of the Eshelby's tensor S for cylindrical, flat elliptic, penny-shaped inclusions. Using these known expressions of S in the equations of $\in_1$ and $\in_2$ for elliptic inclusions, $\in_1$ and $\in_2$ for these shapes can be determined. Thus, YM and PR can also be determined.

The material parameter estimator 120 can also be configured to calculate interstitial permeability and vascular permeability of a material employing strain data and multiple analytical models. The strain data can be the axial strain and the lateral strain of the material. The analytical models relates the interstitial permeability and vascular permeability to the strain data.

First, a time constant $\tau$ of a strain inside an inclusion represented by the strain data is determined employing the strain data and Equation 4.

$$\tau = \frac{a^2}{H_A k x_1} + \frac{1}{H_A \chi} \quad (4)$$

In Equation 4, a is the radius of the inclusion, k is the interstitial permeability of the inclusion, $H_A$ is the aggregate modulus of the inclusion, $\chi$ is the average microfiltration coefficient, and $x_1$ is the root of a Bessel equation depending on the Poisson's ratio of the inclusion. Values of $x_1$ for different Poisson's ratios are known in the art. The interstitial permeability can be determined employing the time constant $\tau$ in Equation 5.

$$k = \frac{a^2}{H_A \tau (\alpha^2 + x_1)} \quad (5)$$

Equation 5 includes a spatial parameter of interstitial fluid pressure (IFP) $\alpha$. In various examples, a spatial parameter of IFP $\alpha$ can be determined from the fluid pressure inside the material employing the strain data. The fluid pressure p can be determined by knowledge of the volumetric strain at two different times as $$p = K(\varepsilon_{v2} - \varepsilon_{v1}),$$

where $$K = \frac{E_i}{3(1 - 2v_i)}$$

is the compression modulus of the material and $\varepsilon_{v2}, \varepsilon_{v1}$ are the volumetric strains at two different times, respectively.

The spatial parameter of IFP $\alpha$ can be determined employing the fluid pressure in Equation 6. A curve fitting algorithm can be used to solve for $\alpha$.

$$p(R) = \Omega\left(1 - \frac{\sinh(\alpha R)}{R \sinh \alpha}\right), \text{ where } \alpha = a\sqrt{\frac{L_p}{k}\frac{S}{V}} \quad (6)$$

Here, $\Omega$ is related to the peak fluid pressure $p_0$, i.e., $p_0 = \Omega(1 - \alpha \operatorname{cosec}(\alpha))$, a is the radius of the inclusion, $L_p$ is the vascular permeability, k is the interstitial permeability and $$\frac{S}{V}$$

is the surface area to volume ratio, which can be determined using methods available in the art. By knowledge of $\alpha$, the ratio between vascular permeability and interstitial permeability $$\frac{L_p}{k}$$

can also be determined using Equation 6, if desired.

From Equation 5, the vascular permeability of the material can be determined employing Equation 7.

$$L_p = \chi \frac{V}{S} = \frac{\alpha^2}{a^2} k \frac{V}{S} = \frac{\alpha^2}{H_A \tau(\alpha^2 + x_n)} \frac{V}{S} \tag{7}$$

In addition to the interstitial permeability and vascular permeability, the SSg of a material can be determined from SSc (compression induced stress inside the material) and the relationships between various mechanical and transport parameters. For example, SSg is theoretically linked to IFP, IFP is theoretically linked to FPc, and FPc is theoretically linked to SSc. The SSc can be determined employing strain data and at least one analytical model, and therefore the SSg with the understanding that the spatial distribution of SSc corresponds to the spatial distribution of SSg, differing, for example, only in peak and boundary values. The radial and circumferential SSc inside the sample (in cylindrical coordinates) may be, in some embodiments, be assumed to be equal in axisymmetric conditions. Therefore, the radial and circumferential SSc components and fluid pressure (FPc) in spherical coordinates may be determined from Equations 8 and 9 below.

$$\sigma_{RR}(R, t) = \sqrt{2\sigma_{rr}^2(\sqrt{r^2+z^2}, t) + \sigma_{zz}^2(\sqrt{r^2+z^2}, t)} \tag{8}$$

$$\sigma_{\theta\theta}(R, t) = \sigma_{rr}(\sqrt{r^2+z^2}, t) \tag{9}$$

Here, $\sigma_{RR}$ and $\sigma_{zz}$ can be computed by knowledge of the applied compression and YM and PR of the inclusion and background.

FPc can be determined employing Equation 10.

$$p(R, t) = p(\sqrt{r^2+z^2}, t) \tag{10}$$

The radial and circumferential SSc and FPc may be normalized by dividing them by an applied pressure used when taking the data.

The normalized SSg (SSn) can be determined using Equation 11.

$$SS_n(R) = 1 - \frac{\sinh(\alpha \frac{R}{a})}{\frac{R}{a}\sinh\alpha} \tag{11}$$

where R is the spherical coordinate.

Equation 12 can be used to compute the surface area to volume ratio of the capillary walls inside the inclusion, for example a tumor.

$$\frac{S}{V} = 10 f V_t^g \tag{12}$$

In Equation 12, $V_t$ is the volume of the inclusion. In spherical inclusions, $V_t$ can be computed as $V_t = 4/3 \pi a^3$, f=54.68, and g=−0.2021. For Equation 12, a is in units of mm and S/V is in units of $cm^{-1}$.

Figure 2:
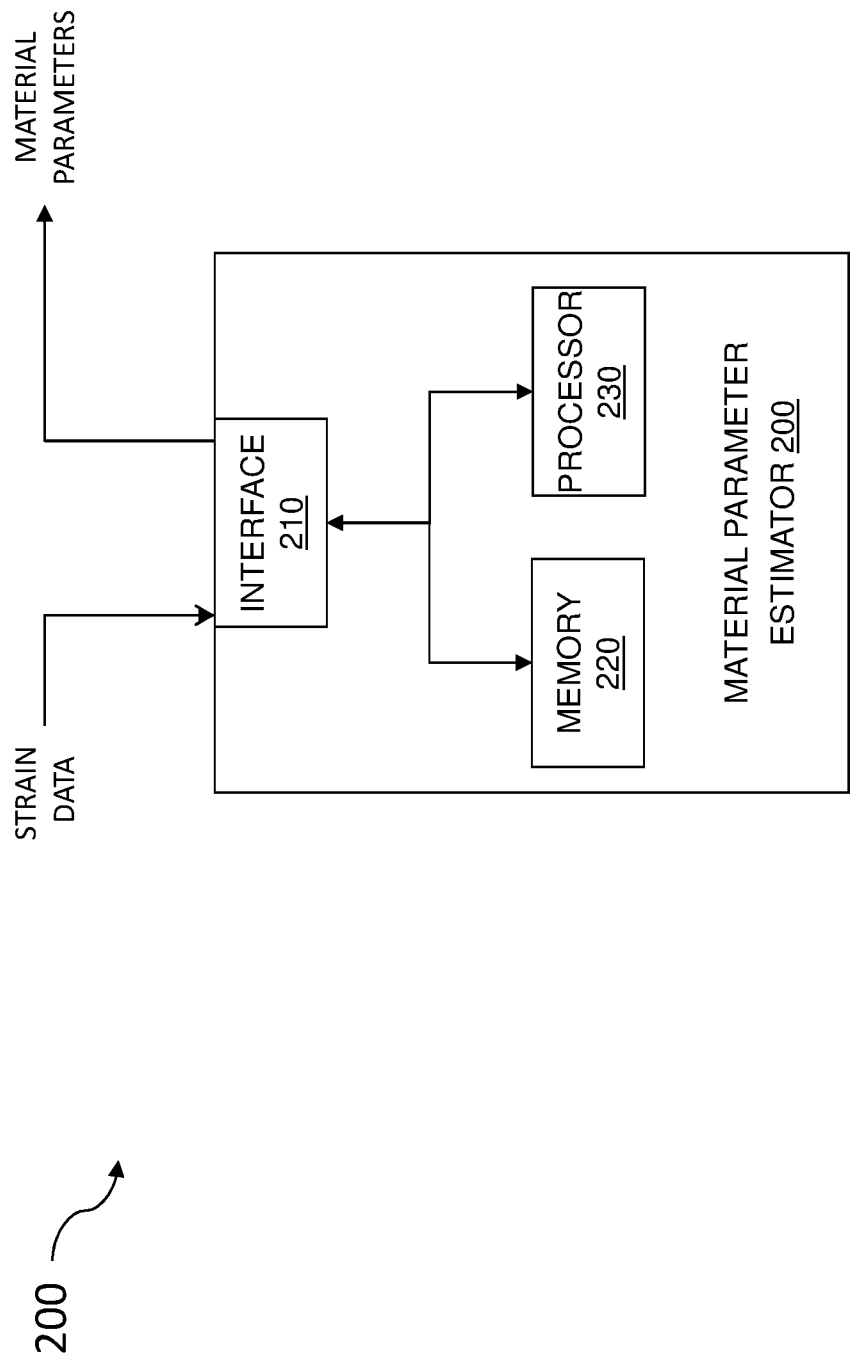
FIG. 2 illustrates a block diagram of an example of a material parameter estimator constructed according to the principles of the disclosure.

FIG. 2 illustrates a block diagram of an example of a material parameter estimator 200 constructed according to the principles of the disclosure. The material parameter estimator 200 is configured to calculate material parameters of material, such as a cancer material, employing strain data and analytical models. The material parameter estimator 200 can be integrated on one or more computing devices or systems. Thus, functions performed by the material parameter estimator 200 can be distributed to different computing devices or systems. For example, some of the functions performed by the material parameter estimator 200 can be performed by a computing device located at a clinic or lab, and other functions can be performed at a data processing center, a computing facility, or another suitable location. As such, the material parameter estimator 200 can be implemented on a server, a cloud service, a tablet, a laptop, a smartphone, other types of computing systems, or a combination thereof.

The material parameter estimator 200 includes an interface 210, a memory 220, and a processor 230. The interface 210 is a component or device interface configured to receive strain data of a material and provide parameters of the material determined by the material parameter estimator 200. The strain data can be obtained from an imaging system or obtained from image data from the imaging system. In some applications, the material parameter estimator 200 can receive the strain data from an imaging system. The strain data can also be obtained via other non-imaging methods.

The material parameters can be sent to a storage device, such as a digital memory storage, provided to a user, such as a clinician, researcher or a lab technician, by sending the material parameters to a user interface, such as a display, or sent to another computing device. The computing device can be remote from the material parameter estimator 200, such as a cloud server connected via a communications network, or proximate the material parameter estimator 200. The interface 210 can be a conventional interface that communicates data according to standard protocols. As such, the interface 210 is configured to communicate data, i.e., transmit and receive data. Accordingly, the interface 210 includes the necessary logic, ports, terminals, connectors, etc., to communicate data. The ports, terminals, connectors, may be conventional receptacles for communicating data via a communications network.

The memory 220 is configured to store the analytical models employed to determine the material parameters from the strain data. Additionally, the memory 220 is configured to store a series of operating instructions that direct the operation of the processor 230 when initiated. At least a portion of the operating instructions can correspond to the analytical models disclosed herein. The memory 220 is a non-transitory computer readable medium.

As such, the memory 220 is a data storage configured to store computer executable instructions to direct the operation of the processor 230 when initiated thereby. The memory can be a non-volatile memory. The memory 220 can also store data, such as the strain data. The operating instructions may correspond to the analytical models or corresponding algorithms that provide the functionality of the techniques or schemes disclosed herein. For example, the operating instructions may correspond to the algorithm or algorithms that, when executed, determine material parameters from strain data.

The processor 230 is configured to direct the operation of the material parameter estimator 200. As such, the processor 230 includes the necessary logic to communicate with the interface 210 and the memory 220 and perform the functions described herein to determine parameters of a material from strain data obtained from the material. For example, the processor 230 is can be configured, e.g., designed and constructed, to perform at least some of the methods represented by FIGS. 3-5.

Figure 3:
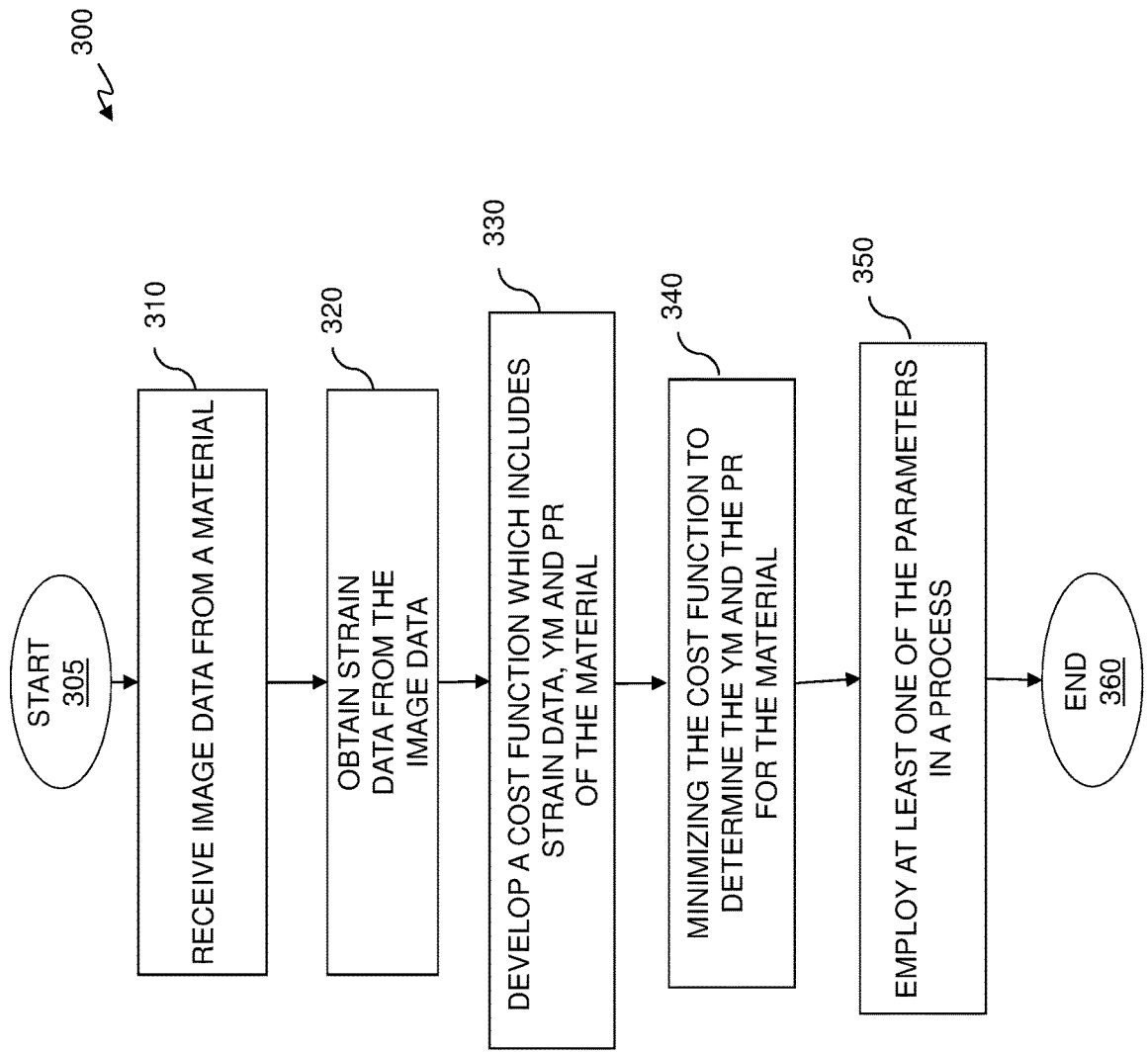
FIG. 3 illustrates a flow diagram of an example of a method that includes estimating parameters inside materials carried out according to the principles of the disclosure.
Figure 4:
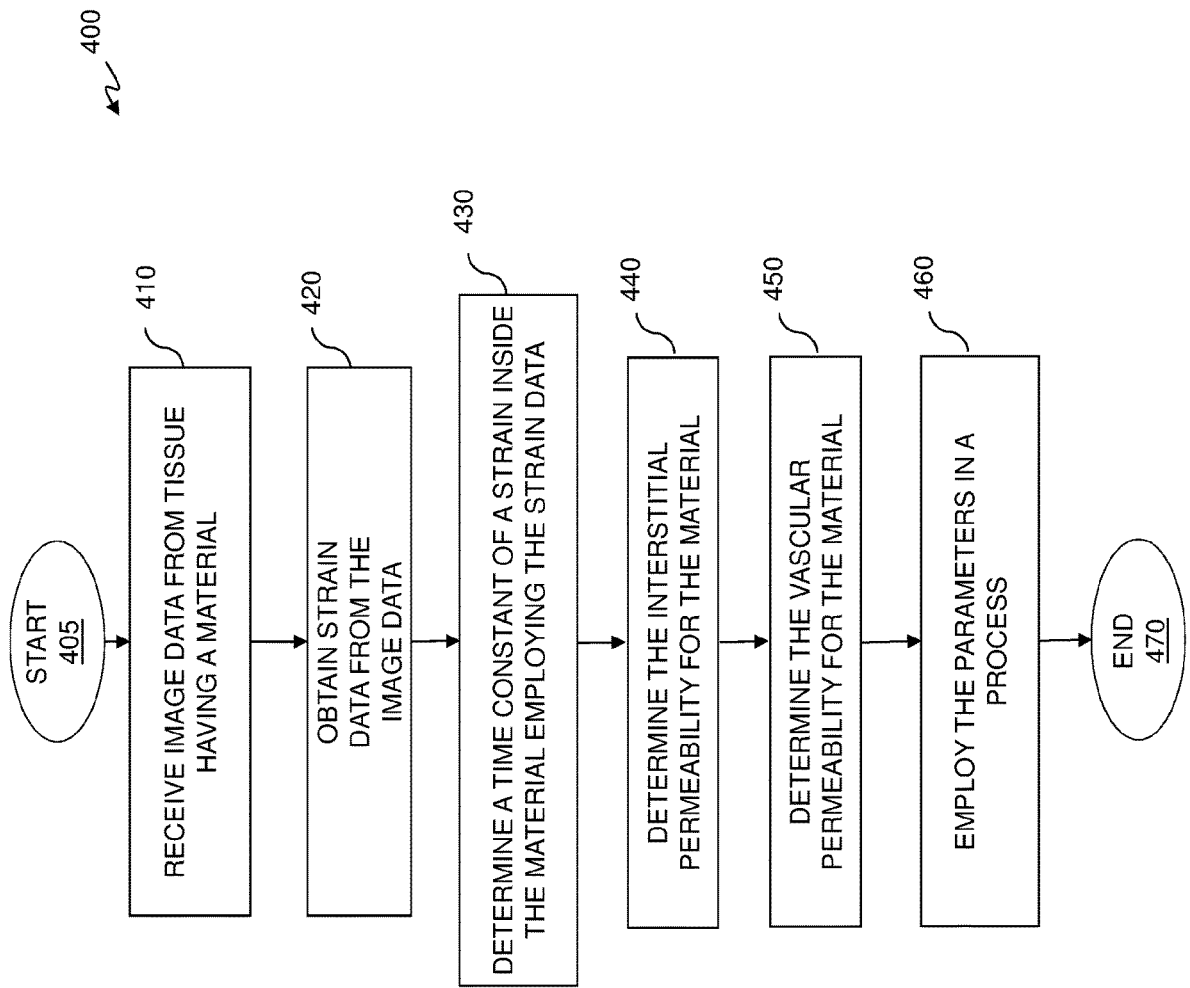
FIG. 4 illustrates a flow diagram of an example of another method that includes estimating parameters inside materials carried out according to the principles of the disclosure.
Figure 5:
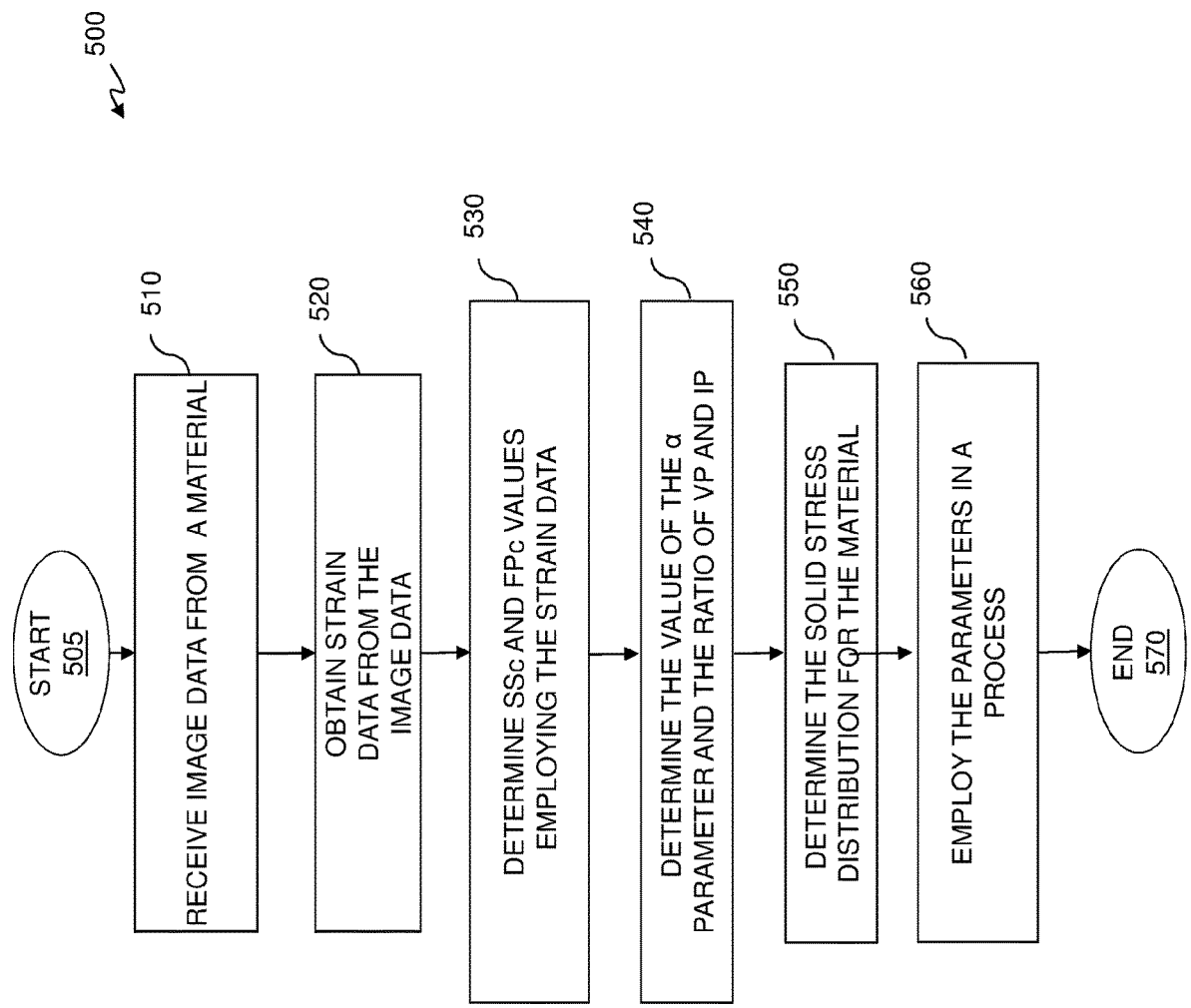
FIG. 5 illustrates a flow diagram of an example of yet another method that includes estimating parameters inside materials carried out according to the principles of the disclosure.

FIGS. 3-5 illustrate flow diagrams of examples of methods for determining parameters of materials using strain data and analytical models, such as represented by the Equations provide herein. FIGS. 3-5 include getting the strain data from image data. As disclosed herein, the strain data can alternatively be obtained via other methods and used with the analytical models.

FIG. 3 illustrates a flow diagram of an example of a method 300 for reconstructing YM and PR parameters inside materials carried out according to the principles of the disclosure. The method 300 is a non-invasive method. In some examples, the method 300 does not use imaging contrast agents. At least some of the steps of the method 300 are performed by a processor, such as the processor 230. The processor can be directed to perform the steps by a computer program product. The method 300 can be carried out by a material parameter estimator such as disclosed herein; for example, the material parameter estimator 200. The method 300 begins in a step 305.

In a step 310, image data is received from a material, such as from tissue sample or a tumor sample or a tissue sample of a human or animal having a tumor. In other examples, the material can be a non-biological tissue. The image data can be obtained from an ultrasound scan. In other examples, image data can be obtained from another type of imaging method, such as mammography, MRI, CT, acoustics or photoacoustic imaging or a combination of imaging methods. An ultrasound poroelastography procedure can be used to obtain the image data.

In a step 320 strain data of the material is obtained from the imaging data. The strain data can be estimated from the image data via conventional methods such as sample tracking, correlation, optical flow estimation, block matching, Doppler-based processing, etc. In some examples, the strain data can be obtained from multiple images at different times. The strain data can be axial and lateral strain data.

In a step 330 a first analytical model is employed that includes the strain data, YM, and PR of the material. Equation 1 provided above is an example of a cost function that can be employed as the first analytical model.

In a step 340, the YM and the PR of the material are reconstructed employing the first analytical model. A second analytical model can be employed with the first analytical model for the reconstructing. Continuing the example of Equation 1, YM and PR can be reconstructed by minimizing the cost function employing Equation 2. The reconstructing can be performed without imposing assumptions on boundary conditions of the material. In some examples, the reconstructing is only based on the strain data, known values of applied stress on the material, and geometry of the material. The YM and the PR can be reconstructed or determined at each pixel inside the material, both simultaneously and independently. At least some of the pixels can be determined in parallel, or at least partially in parallel, employing a parallel processor.

At least one of the material parameters is employed in a process, such as a medical or research or industrial process, in a step 350. The material parameter can be provided to a user for application in various medical, non-medical, industrial, or research processes. The user can be a clinician, doctor, researcher, technician, imaging expert, nurse, or other medical or non-medical or research personnel. The parameter can be provided to a user or users by various user interfaces. For example, a visual display can be used. The different processes include the diagnosis, prognosis and treatment of cancers. Knowledge of the values of YM in cancers can be used by a doctor to determine the cancer stage and sometimes cancer metastasis. PR can be beneficial for monitoring cancer-related diseases such as lymphedema. Both YM and PR can be employed to estimate other important properties, such as interstitial fluid pressure, interstitial permeability and vascular permeability, of a material, such as a tumor. The method 300 continues to step 360 and ends.

FIG. 4 illustrates a flow diagram of an example of a method 400 for estimating interstitial permeability and vascular permeability inside materials carried out according to the principles of the disclosure. The method 400 is a non-invasive method that does not, for example, use imaging contrast agents. At least some of the steps of the method 400 are performed by a processor, such as the processor 230 of FIG. 2. The processor can be directed to perform the steps by a computer program product. The method 400 can be carried out by a material parameter estimator such as disclosed herein. The method 400 begins in a step 405.

In a step 410, image data is received from a material, such as from a tissue sample of a human or animal having a tumor. The image data can be obtained from an ultrasound scan. In other examples, image data can be obtained from another type of imaging method, such as mammongraphy, MRI, CT, acoustics, photoacoustic imaging or a combination of imaging methods. An ultrasound poroelastography procedure can be used to obtain the image data.

In a step 420, strain data of the material is obtained from the imaging data. The strain data can be estimated from the image data via conventional methods such as sample tracking, correlation, optical flow estimation, block matching, Doppler-based processing, etc. In some examples, the strain data can be obtained from multiple images at different times. The strain data can be axial and lateral strain data of the material.

In a step 430 a time constant of a strain inside the material represented by the strain data is determined employing the strain data and a first analytical model. The first analytical model for method 400 can be Equation 4 provided above.

An interstitial permeability is determined in a step 440 employing the time constant in a second analytical model. The second analytical model can be Equation 5 provided above. Equation 5 includes a spatial parameter of IFP $\alpha$. The interstitial permeability can be determined via Equation 5 with a known spatial parameter of IFP $\alpha$. In various examples, a spatial parameter of IFP $\alpha$ can be determined from the fluid pressure inside the material employing the strain data. For determining the fluid pressure, the volumetric strain can be calculated at two different times. For example, the volumetric strain can be calculated at 10 seconds and at 60 seconds.

Employing a third analytical model, the spatial parameter of IFP $\alpha$ can be determined employing the fluid pressure. The third analytical model for method 400 can be Equation 6. A curve fitting algorithm can be used to solve for $\alpha$. In some examples, $\alpha$ and a peak fluid pressure can be made floating when using the curve fitting algorithm.

In a step 450, vascular permeability of the material is determined. A fourth analytical model of method 400 can be used to determine the vascular permeability. The fourth analytical model can be Equation 7 provided above.

At least one of the interstitial permeability or vascular permeability is employed in a process, such as a medical or industrial or research process, in a step 460. The permeabilities can be provided to a user for application in various medical or non-medical or industrial or research processes. The user can be a clinician, doctor, researcher, technician, imaging expert, nurse, or other medical or non-medical or research personnel. The permeability can be provided to a user or users by various user interfaces. For example, a visual display can be used. The different processes include the diagnosis, prognosis and treatment of cancers. The method 400 continues to step 470 and ends.

FIG. 5 illustrates a flow diagram of an example of a method 500 for estimating SSg inside material carried out according to the principles of the disclosure. The method 500 can be a non-invasive method that does not use imaging contrast agents. At least some of the steps of the method 500 are performed by a processor, such as the processor 230 of FIG. 2. The processor can be directed to perform the steps by a computer program product. The method 500 can be carried out by a material parameter estimator such as disclosed herein. The method 500 begins in a step 505.

In a step 510, image data is received from a material, such as from a tissue sample, tumor sample or a tissue sample of a human or animal having a tumor. The image data can be obtained from an ultrasound scan. In other examples, image data can be obtained from another type of imaging method, such as mammography, CT, MRI, acoustics, photoacoustic imaging or a combination of imaging methods. An ultrasound poroelastography procedure can be used to obtain the image data.

In a step 520, strain data of the material is obtained from the imaging data. The strain data can be estimated from the image data via conventional methods such as sample tracking, correlation, optical flow estimation, block matching, Doppler-based processing, etc. In some examples, the strain data can be obtained from multiple images at different times. The strain data can be axial and lateral strain data of the material.

In a step 530, SSc and FPc values are calculated using the strain data and at least one analytical model. Analytical models represented by Equations 8, 9, 10 and 11 can be employed to determine SSc and FPc values. The radial and circumferential SSc inside a material (in cylindrical coordinates) may, in some embodiments, be assumed to be equal in axisymmetric conditions. Therefore, the radial and circumferential SSc components and the FPc in spherical coordinates may be determined from the SSc components and FPc in cylindrical coordinates. In some embodiments, estimation of YM and PR of the inclusion and background, such as via the method 300, can be employed for determining SSc and FPc. Other methods for estimating YM and PR can also be used. In some examples, the radial and circumferential SSc and FPc may be normalized by dividing them by an applied pressure used when taking the data such that the values correspond, in some embodiments, to 1 kPa of applied pressure.

In a step 550, the solid stress distribution SSg is determined. The SSg can be determined based on the spatial distribution of SSc inside the material and the calculations and determinations made in step 530.

At least one of the parameters is employed in a process in a step 560. For example, the SSg can be employed in a medical or industrial or research process in step 560. The SSg can be provided to a user for application in various medical or industrial or research processes. The user can be a clinician, doctor, researcher, technician, imaging expert, nurse, or other medical or non-medical or research personnel. The SSg can be provided to a user or users by various user interfaces. For example, a visual display can be used. The different processes include the diagnosis, prognosis and treatment of diseases such as cancers. The method 500 continues to step 570 and ends.

A portion of the above-described apparatus, systems or methods may be embodied in or performed by various analog or digital data processors or computers, wherein the computers are programmed or store executable programs of sequences of software instructions to perform one or more of the steps of the methods. The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods, or functions, systems or apparatuses described herein. Portions of disclosed embodiments may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

Those skilled in the art to which this application relates will appreciate that other and further additions, deletions, substitutions and modifications may be made to the described embodiments.

Various aspects of the disclosure can be claimed including the apparatuses, systems, computer program products, and methods as disclosed herein including:

A. A non-invasive method for simultaneously estimating Young's modulus (YM) and Poisson's ratio (PR) of materials, including: (1) receiving image data from the material, (2) obtaining strain data from the image data, and (3) reconstructing the YM and the PR of the material based on the strain data at a steady state.

B. A material parameter estimator, including: (1) an interface configured to receive data of a material, and (2) a processor configured to determine YM and PR of the material employing strain data determined from the data and a cost function corresponding to the YM and the PR.

C. A non-invasive method for estimating the interstitial permeability and vascular permeability of materials, including: (1) obtaining strain data of a material, (2) calculating a time constant of the strain data employing a first analytical model, and (3) determining interstitial permeability of the material employing the time constant in a second analytical model.

D. A material parameter estimator, including: (1) an interface configured to receive strain data of a material, and (2) a processor configured to calculate a time constant of the strain data employing a first analytical model and calculate interstitial permeability of the material employing the time constant in a second analytical model.

E. A non-invasive method for estimating parameters of materials, including: (1) obtaining strain data of a material, (2) calculating a compression induced solid stress distribution (SSc) and a fluid pressure (FPc) inside the material employing the strain data in a first analytical model, (3) determining spatial parameter of interstitial fluid pressure (IFP) α using a second analytical model employing the fluid pressure, (4) determining a ratio of vascular permeability (VP) to interstitial pressure (IP) employing the fluid pressure in a third analytical model, and (5) determining a solid stress (SSg) distribution inside the material based on the calculated α.

F. A material parameter estimator, including: (1) an interface configured to receive strain data of a material and (2) a processor configured to calculate material parameters of the material employing strain data determined from the data and multiple analytical models and determine SSg based on the calculated material parameters.

Each of aspects A to F can have one or more of the following additional elements in combination.

Element 1: wherein the material is a biological tissue. Element 2: wherein the material is a tumor. Element 3: wherein the reconstructing is based on minimizing a cost function representing the YM and the PR. Element 4: further comprising developing the cost function. Element 5: wherein the reconstructing is performed without imposing assumptions on boundary conditions of the material. Element 6: wherein the reconstructing is based on the strain data, known values of applied stress on the material, and geometry of the material. Element 7: wherein the reconstructing includes reconstructing the YM and the PR at each pixel inside the material simultaneously and independently. Element 8: wherein the image data is obtained from an ultrasound scan. Element 9: wherein the ultrasound scan is an ultrasound poroelastography experiment. Element 10: wherein the processor is configured to determine the YM and the PR simultaneously employing the cost function. Element 11: wherein the processor is configured to simultaneously determine the YM and the PR by minimizing the cost function. Element 12: wherein the processor is configured to determine the YM and the PR of the material based on the strain data at a steady state. Element 13: wherein the cost function can be based on eigen strain formulations. Element 14: wherein the processor is further configured to determine the YM and the PR without imposing assumptions on boundary conditions of the material. Element 15: wherein the processor is configured to determine the YM and the PR by reconstructing the YM and the PR at each pixel inside the material simultaneously and independently. Element 16: wherein the strain data includes axial and lateral strain data. Element 17: further comprising determining vascular permeability employing a third analytical model. Element 18: wherein the strain data includes normal strain data inside the material. Element 19: wherein the strain data is from image data of the material. Element 20: wherein the image data is obtained from an ultrasound scan. Element 21: wherein the ultrasound scan is an ultrasound poroelastography experiment. Element 22: wherein the determining includes using a curve fitting technique on a temporal profile of the strain data. Element 23: wherein the determining the vascular permeability includes using a curve fitting technique on a temporal profile of the strain data. Element 24: wherein the strain data is obtained from an ultrasound poroelastography procedure. Element 25: wherein the processor is configured to calculate vascular permeability of the material employing a third analytical model. Element 26: wherein the processor is configured to determine interstitial permeability employing a curve fitting algorithm. Element 27: wherein the processor is configured to determine the vascular permeability employing a curve fitting algorithm. Element 28: wherein the strain data includes axial strain inside the material. Element 29: wherein the strain data is obtained without employing a contrast agent. Element 30: wherein the strain data includes normal strain data. Element 31: wherein the determining spatial parameter of interstitial fluid pressure (IFP) α includes employing a curve fitting algorithm. Element 32: wherein the curve fitting algorithm includes varying a peak value, a boundary value. Element 33: wherein the determining the VP to IP ratio includes employing a curve fitting algorithm. Element 34: wherein the curve fitting algorithm includes varying a peak value, a boundary value, and α. Element 35: wherein the strain data is obtained from image data. Element 36: wherein the image data is obtained from an ultrasound scan via an ultrasound poroelastography experiment. Element 37: wherein the strain data is obtained from an image via an ultrasound scan of the material. Element 38: wherein the ultrasound scan is an ultrasound poroelastography experiment. Element 39: wherein the processor is configured to calculate a compression induced solid stress distribution (SSc) and a fluid pressure (FPc) inside the material employing the volumetric strain data in a first analytical model. Element 40: wherein the processor is further configured to determine a spatial parameter of interstitial fluid pressure (IFP) α using a second analytical model employing the fluid pressure. Element 41: wherein the processor is further configured to determine a ratio of vascular permeability (VP) to interstitial permeability (IP) employing the fluid pressure in a third analytical model and determine a solid stress (SSg) distribution inside the material based on the calculated SSc, FPc, α, and the VP to IP ratio. Element 42: wherein the processor is configured to determine α employing a curve fitting algorithm. Element 43: wherein the curve fitting algorithm includes varying a peak value, a boundary value.

The invention claimed is:

1. A non-invasive method for simultaneously estimating Young's modulus (YM) and Poisson's ratio (PR) of materials, comprising:
generating, using an ultrasound device, radio frequency (RF) signals from a material at different times;
acquiring, from the RF signals, strain data when the material is at a steady state;
simultaneously reconstructing, at the different times, the YM and the PR of the material by minimizing a cost function including the YM and the PR using the strain data of the material and a processor, wherein the cost function represents a difference between multiple eigenstrain measures along multiple different spatial directions related to a position of the material, wherein the eigenstrain measures are defined by $\epsilon^*_1$ and $\epsilon^*_2$, wherein the $\epsilon^*_1$ is defined by a product of an inverse of Eshelby's tensor S and the strain data and the $\epsilon^*_2$ is defined by a multiplication of an inverse of an addition of a tensor A and Eshelby's tensor S and the strain data, wherein the tensor A involves matrices representing stiffness properties of the material;
generating, using the YM and the PR, YM and PR maps corresponding to pixels of the material for each of the different times using the strain data acquired from the RF signals of the ultrasound device; and
monitoring the material over the different times using the YM maps or the PR maps.

2. The method as recited in claim 1 wherein the material is a biological tissue.

3. The method as recited in claim 1, wherein the material is a tumor and the method further includes monitoring a treatment of the tumor using the YM maps or the PR maps.

4. The method as recited in claim 3, wherein the treatment is vascular normalization, stress normalization, chemotherapy, or immunotherapy.

5. The method as recited in claim 1, wherein the material is a tumor and the method further includes monitoring lymphedema using at least one of the YM and the PR maps.

6. The method as recited in claim 1, wherein the material is a non-biological material.

7. The method as recited in claim 1, further comprising displaying at least one of the YM maps or the PR maps.

8. The method as recited in claim 1, wherein the simultaneously reconstructing is performed by a parallel processor and includes reconstructing the YM and the PR at each pixel of the material simultaneously and independently.

9. The method as recited in claim 1, wherein the ultrasound system is an ultrasound poroelastography system.

10. A diagnostic device for quantifying material properties, comprising:
an interface configured to receive radio frequency (RF) signals of a material, wherein the RF signals are obtained at different times using an ultrasound device when the material is at steady state;
a processor configured to perform operations that include
acquiring, from the RF signals, strain data when the material is at a steady state;
simultaneously reconstructing, at the different times, Young's modulus (YM) and Poisson's ratio (PR) of the material by minimizing a cost function including the YM and the PR using the strain data of the material, wherein the cost function represents a difference between multiple eigenstrain measures along multiple different spatial directions related to a position of the material, wherein the eigenstrain measures are defined by $\epsilon^*_1$ and $\epsilon^*_2$, wherein the $\epsilon^*_1$ is defined by a product of an inverse of Eshelby's tensor S and the strain data and the $\epsilon^*_2$ is defined by a multiplication of an inverse of an addition of a tensor A and Eshelby's tensor S and the strain data, wherein the tensor A involves matrices representing stiffness properties of the material; and
generating, using the YM and the PR, YM and PR maps corresponding to pixels of the material for each of the different times using the strain data acquired from the RF signals of the ultrasound device.

11. The diagnostic device as recited in claim 10, wherein the processor is a parallel processor and the simultaneously reconstructing includes independently reconstructing the YM and the PR at each pixel of the material.

12. The diagnostic device as recited in claim 10, wherein the strain data includes axial and lateral strain data.

13. The diagnostic device as recited in claim 10, wherein the ultrasound device is an ultrasound poroelastography device.

14. The diagnostic device as recited in claim 13 wherein the strain data is obtained without employing a contrast agent.

15. A system configured to estimate Young's modulus (YM) and Poisson's ratio (PR) of materials, the system comprising:
an ultrasound system configured to obtain radio frequency (RF) signals from a material at different times;
a processor configured to perform operations including:
acquiring, from the RF signals, strain data when the material is at a steady state; and
simultaneously reconstructing, at the different times, the YM and the PR of the material by minimizing a cost function including the YM and the PR using the strain data of the material, wherein the cost function represents a difference between eigenstrain measures along different spatial directions related to a position of the material, wherein the eigenstrain measures are defined by $\epsilon^*_1$ and $\epsilon^*_2$, wherein the $\epsilon^*_1$ is defined by a product of an inverse of Eshelby's tensor S and the strain data and the $\epsilon^*_2$ is defined by a multiplication of an inverse of an addition of a tensor A and Eshelby's tensor S and the strain data, wherein the tensor A involves matrices representing stiffness properties of the material, and
generating, using the YM and the PR, YM and PR maps that correspond to pixels of the material for each of the different times using the strain data acquired from the RF signals of the ultrasound system; and
a display configured to visually present the YM maps and the PR maps.

16. The method as recited in claim 15, further comprising monitoring the material using the displayed YM maps or PR maps.

* * * * *